(12) United States Patent
Bleunven et al.

(10) Patent No.: US 11,134,960 B2
(45) Date of Patent: Oct. 5, 2021

(54) LOCKABLE SURGICAL SYSTEM

(71) Applicant: GANYMED ROBOTICS, Paris (FR)

(72) Inventors: Blaise Bleunven, Paris (FR); Cyril Moulin, Argonay (FR); Sophie Cahen, Paris (FR); Nicolas Loy Rodas, Puteaux (FR); Michel Bonnin, Lyons (FR); Tarik Ait Si Selmi, Lyons (FR); Marion Decrouez, Sèvres (FR)

(73) Assignee: GANYMED ROBOTICS, Paris (FR)

( * ) Notice: Subject to any disclaimer, the term of this patent is extended or adjusted under 35 U.S.C. 154(b) by 0 days.

(21) Appl. No.: 16/887,279

(22) Filed: May 29, 2020

(65) Prior Publication Data

US 2020/0375611 A1 Dec. 3, 2020

Related U.S. Application Data

(60) Provisional application No. 62/855,039, filed on May 31, 2019.

(51) Int. Cl.

| | |
|---|---|
| *A61B 17/58* | (2006.01) |
| *A61B 17/60* | (2006.01) |
| *A61F 2/00* | (2006.01) |
| *A61B 17/15* | (2006.01) |
| *A61B 34/20* | (2016.01) |
| *A61B 34/30* | (2016.01) |
| *A61B 17/16* | (2006.01) |

(52) U.S. Cl.
CPC .......... *A61B 17/157* (2013.01); *A61B 17/155* (2013.01); *A61B 17/1675* (2013.01); *A61B 34/20* (2016.02); *A61B 34/30* (2016.02); *A61B 2034/2065* (2016.02)

(58) Field of Classification Search
CPC combination set(s) only.
See application file for complete search history.

(56) References Cited

U.S. PATENT DOCUMENTS

| | | | |
|---|---|---|---|
| 5,403,319 A | * | 4/1995 | Matsen, III ............ A61B 17/15 606/88 |
| 6,554,837 B1 | | 4/2003 | Hauri et al. |
| 2005/0021039 A1 | | 1/2005 | Cusick et al. |

(Continued)

FOREIGN PATENT DOCUMENTS

| | | |
|---|---|---|
| EP | 1635715 A1 | 3/2006 |
| EP | 1755466 A1 | 2/2007 |
| EP | 1444957 B1 | 3/2007 |

(Continued)

*Primary Examiner* — Sameh R Boles
(74) *Attorney, Agent, or Firm* — Maier & Maier, PLLC (57) ABSTRACT

A surgical system including a machining tool aimed at being manually displaced by an operator, a lockable unit including at least two linked and manually displaceable elements aimed at being manually arranged according to a least one calculated locked configuration, a sensor unit including at least one sensor aimed at following, in real time, a real time configuration of the lockable unit within an anatomical reference system, —where the at least two elements of the lockable unit cooperate with lockable element, the lockable element being configured to be activated by a control unit when the real time configuration of the lockable unit corresponds to the at least one locked configuration recorded inside the control unit.

12 Claims, 7 Drawing Sheets

(56) References Cited

U.S. PATENT DOCUMENTS

2006/0122617 A1    6/2006  Lavallee et al.
2006/0200161 A1    9/2006  Plaskos et al.

FOREIGN PATENT DOCUMENTS

| EP | 1669033 B1 | 2/2009 |
|----|------------|--------|
| FR | 3033691 A1 | 9/2016 |
| WO | 2005/122916 A1 | 12/2005 |

* cited by examiner

LOCKABLE SURGICAL SYSTEM

FIELD

The present invention relates to the field of surgical robots. In particular, the present invention relates to the field of controlling the positioning of a machining tool during a surgical operation.

BACKGROUND

A first family of mechanical guide solutions for machining tools for bone cutting is known from the state of the art. Patent FR3033691 describes a device for the preparation of bone cuts for the establishment of a knee prosthesis without conservation of the cruciate ligaments, comprising a femoral cutting guide and a tibial cutting guide made to measure. Said device is based on scan data of the patient's joint which is transmitted to a planning software. Each guide has supporting means on the distal femoral epiphysis and on the proximal tibia I epiphysis, in two substantially orthogonal planes, and arrangements for the passage of drill guides, and at least one cutting blade. According to this solution, the cutting planes are determined digitally in the femur and tibia reference systems. These cutting planes then determine the configuration of the two guides, which are used after being firmly attached to the bone to be machined. It is necessary to screw the guide to the bone to allow effective guidance of the tool. This solution is very invasive due to the requirement of mechanical coupling of the bone with the guide, and requires the manufacture of a specific guide for each operation. Such a solution also leads the surgeon to spend a lot of time to mechanically couple the bone with the guide in several successive positions to perform the various cuts.

U.S. Pat. No. 6,554,837 describes a positioning device with a base that attaches to the bone. This positioning device is driven by computer-controlled motors. In the European patent EP 1 444 957 the position of the device is determined by a navigation system. A tracking system is used in combination with the navigation system, allowing the correct positioning and orientation of the implants. The main disadvantage of the positioning devices described above is that they are based on an anchoring element or a base component that must first be attached to the bone. Said devices also comprise an important amount of positioning elements that connect the cutting guide to the base to adjust the angle and/or position the cutting guide relative to the base with at least 1 and up to 6 degrees of freedom. These types of devices therefore generally take up significant space in the vicinity of the bone and are invasive to the patient. In addition, since an anchor or a base component is first attached to the bone, such positioning devices can cause unnecessary damage or even fracture the bone. In addition, the installation of such positioning devices is usually time-consuming because it must be carried out very precisely and repeatedly for each guide.

Another family of solutions consists in using markers fixed both to the bone and to the guide. The position of the guide relative to the bone is then tracked in real-time from the position and orientation of these markers determined by a stationary sensor. The European patent EP1669033 describes an example of the use of such a device for positioning a bone cutting guide. However, locating the effective position of the device requires uninterrupted acquisition of the position and orientation of markers associated with the device. This is very time and energy consuming, not least because the physician must constantly be aware of his movements in order to not block the necessary "line of sight" from the stationary sensor to the markers.

Patent EP1635715B1 describes another solution for a guiding device for bone cutting adapted to cut bone portions at the level of the head of a bone, comprising: a device with a seat intended to be screwed to the bone at the level of said head, means for adjusting the inclination of a first axis of rotation with respect to said seat around two perpendicular axes OX,OY, an arm, one end of said arm being pivotally assembled on said seat according to the first axis of rotation; and a guide intended to support the tool. This guide is pivotally assembled on the arm according to a second axis of rotation.

A major drawback of such a system is that the fixation of the seat to the femur is quite invasive since it requires implanting large pins into the bone to bear the weight of the robot and compensate for forces exerted during sawing by the saw inserted in the cutting block carried by the robot. Large pins used to carry an important weight and react to important forces can potentially generate bone fracture. In addition, weight and efforts can lead to motion of the pins in the bone, which will impact significantly the accuracy of the system. Besides, the rotational axes have to be adjusted very precisely in order to achieve all the target planes. However, this adjustment is difficult and prone to errors or inaccuracies because it is done manually and is guided through visual feedback provided by the navigation system. If the cutting plane slightly moves during sawing because of the forces exerted by the operator or the saw, it would be very difficult for the operator to detect it and to correct these adjustments manually. Moreover, if the pins are not placed in a correct location because of surgical constraints, anatomical constraints or misuse, the robot will not be able to position the cutting block so that all the cuts can actually be reached, and it will be necessary to reposition the pins in the bone at slightly different locations, which is a difficult task. In addition, this system does not allow carrying out the tibial cut while the seat is fixed to the femur, and therefore another specific device is necessary to perform cuts on the tibia, which takes additional time, pins, systems and efforts.

The reference system of a bone element is usually determined in an invasive and approximate manner. The medullar canal is sometimes used in prior art solutions to provide a reliable reference system, but these solutions require the highly invasive insertion of a rod into the bone canal. Other reference systems are theoretically known, but are generally not accessible on the patient, for whom the amplitude of the incision and therefore of the exposed area is minimized Finally, orthopedics applications require high precision machining on complex surfaces. An error of a fraction of a millimeter or a degree of inclination of the cutting plane for the installation of a knee prosthesis can lead to instability, severe residual pain, walking difficulties and/or prosthesis revision surgery.

As outlined above, there is a need for a less invasive, more compact and surgeon-friendly device, that can be smoothly integrated to the surgical workflow and thus become a standard surgical technique. The present disclosure addresses the aforementioned limitations of the existing surgical robots through a new design that will be described hereafter.

SUMMARY

In order to remedy the disadvantages of the prior art, most notably to offer a less invasive more compact and more intuitive solution, the present invention relates to a surgical system for machining an anatomical structure of a patient positioned on an operation table, said anatomical structure being part of an anatomical reference system of the surgical system, said surgical system comprising:
- a base unit aimed at being secured to the operation table,
- a machining tool aimed at being manually displaced by an operator,
- a lockable unit carried by the base unit, said lockable unit including:
  - at least two linked and manually displaceable elements aimed at being manually arranged according to a least one, relatively to the anatomical structure, calculated locked configuration, said locked configuration being defined within the anatomical reference system, and
  - a constraining device aimed at supporting and guiding the machining tool,
- a grasping element carried by the base unit, said grasping element being designed to secure the anatomical structure the lockable unit and the grasping element being carried by the base unit,
- a sensor unit including at least one sensor aimed at following, in real time, a real time configuration of the lockable unit within the anatomical reference system,
- a control unit containing a recording of the at least one locked configuration of the lockable unit, where the at least two elements of the lockable unit are linked to each other by at least one degree of freedom aimed at cooperating with lockable means, said lockable means being configured to be activated by the control unit when the real time configuration of the lockable unit corresponds to the at least one locked configuration recorded inside the control unit, in order to lock the constraining device in a determined position which constrains the machining tool within a determined machining plan.

Constraining the movement of the lockable unit and therefore the surgical machining tool within a manually induced trajectory improves the accuracy and safety of the procedure.

The system being manually moved is not motorized or automatically actuated and this allows:
- a much leaner and easier control of the tool, as actuators are more complex to integrate and to control and bulkier for similar torque resistance,
- a more affordable device, as locking means are usually cheaper than actuators,
- An increased precision of the trajectory as locking means are direct drive equivalent, meaning without transmission nor gears, compared to actuators.

According to alternative embodiments taken alone or in any technically feasible combination, the system also has several of the following characteristics:
- the control unit is configured to activate each locking means in a progressive way,
- each displaceable element of the lockable unit has a determined position within the locked configuration of the lockable unit, the activation of each locking means being reversely proportional to a distance separating each displaceable element from its determined position,
- the locking means are activated one by one according to a predetermined order recorded inside the control unit,
- the control unit contains at least two locked configurations, said at least two locked configurations being recorded inside the control unit according to a given chronological order, the control unit being configured to activate the locking means according to each locked configuration following the chronological order,
- each locked configuration of the lockable unit corresponds to a unique machining plan, each locked configuration constraining the machining tool within said corresponding unique machining plan,
- the constraining device is a planar mechanism,
- the constraining device is a cutting guide,
- the grasping element includes at least two parts, a first part configured to be rigidly secured to the Femur of the anatomical structure, and a second part being carried by the base unit, said first part being a mobile part aimed at being attached and detached at least two times to the second part,
- the grasping element includes a third part, said third part also being configured to be rigidly secured to the Tibia of the anatomical structure, said third part being another mobile part aimed at being attached and detached at least two times to the second part,
- the anatomical structure includes a first bone and a second bone, the first part of the grasping element being configured to be secured to the first bone and the third part of the grasping element being configured to be secured to the second bone,
- the second part of the grasping element connects either the first part or the third part.

Definitions

In the present invention, the following terms have the following meanings:

"Machining" refers to the mechanical process of cutting or other methods for removing material. The purpose of machining is to modify the dimensions, precision, geometry and surface state of all the surfaces of the finished element, in order to move from a raw original state to a final state in accordance with a predefined model.

"Pose estimation" refers to the estimation of the position and orientation of the device relative to the anatomical structure to be machined. This determination can be carried out either by acquiring an image or a point cloud followed by a digital processing, or by knowing the a priori geometry of the grasping element base and the morphology of the surface of the element to be machined.

"Reference position" refers to a position and orientation of the machining tool in the reference system of the element to be machined and from which the machining head of this tool must move. In other words, the tool is placed in a position and orientation known as the reference position and held in this position for subsequent machining by moving the machining head.

BRIEF DESCRIPTION OF THE DRAWINGS

The following detailed description will be better understood when read in conjunction with the drawings. For the purpose of illustrating, the surgical system is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings in which.

DETAILED DESCRIPTION

While various embodiments have been described and illustrated, the detailed description is not to be construed as being limited hereto. Various modifications can be made to the embodiments by those skilled in the art without departing from the true spirit and scope of the disclosure as defined by the claims.

Figure 1A:
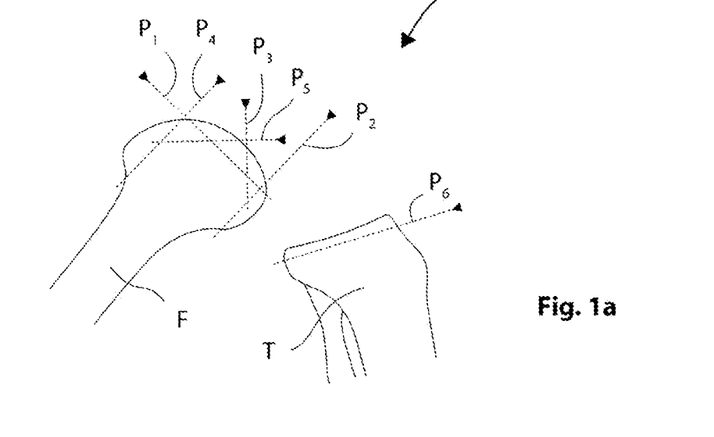
FIG. 1a is a schematic view of an anatomical structure to be machined and of six independent machining planes according to the current invention.
Figure 1B:
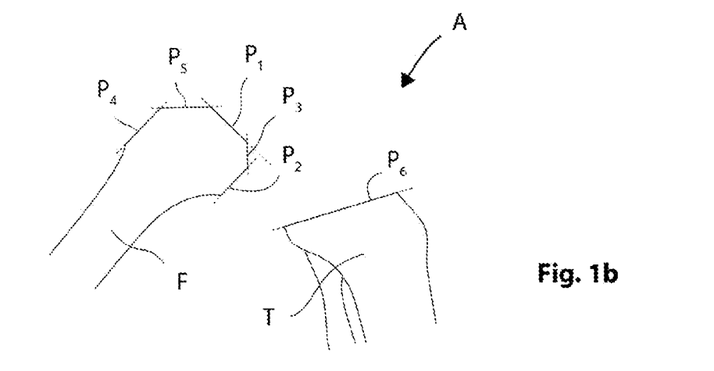
FIG. 1b is a schematic representation of the anatomical structure once machined.
Figure 1C:
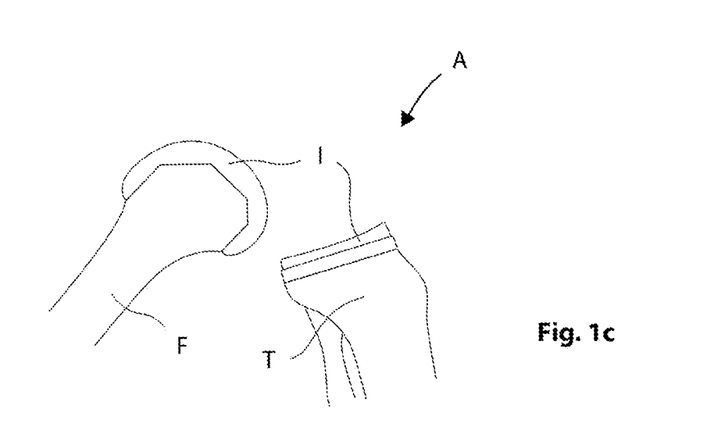
FIG. 1c is a schematic representation of the anatomical structure once the implant has been fixed.

As shown in FIG. 1, an anatomical structure A which is classically well known for regularly needing surgery, is the knee joint. As known per se, the knee joint includes three bones, the femur F and the tibia T and the patella. (We willfully exclude the patella, from this description for it adds no explanatory value). The examples described in the present specification relate therefore to the field of orthopedic surgery and more specifically to the preparation of a femur F and a tibia T for the implantation of a femoral and tibial knee implants I (see FIG. 3).

This preparation includes a succession of well-known steps, each step being the machining of one of the bones F, T according to a given pre-determined machining plane $P_1$, $P_2$, $P_3$, $P_4$, $P_5$, $P_6$ (see FIG. 1). Those machining steps are well-known per se and they usually take place in the same order, depending on the strategy adopted by the operator (surgeon). On FIG. 1, each machining plane $P_1$, $P_2$, $P_3$, $P_4$, $P_5$, $P_6$ is numbered in the generally admitted chronological sequence. Those machining planes $P_1$, $P_2$, $P_3$, $P_4$, $P_5$, $P_6$ are classically determined by a pre-operative surgical planning A pre-operative surgical planning is only valid for one given patient for one given surgery for one given type of implant (size, design, brand, etc.). Each patient (and each surgery) gets a personalized surgical planning. Therefore, the machining planes $P_1$, $P_2$, $P_3$, $P_4$, $P_5$, $P_6$ slightly change for each surgery. The usual first step of the pre-operative surgical planning, is the establishing of a three-dimensional bones F, T model. One way to obtain such a three-dimensional bones F, T model is to use medical imaging such as computed tomography, X-rays, MRI, fluoroscopy, ultrasound or other imaging means. X-ray or scanner, or even MRI, acquisitions are usually made during full weight-bearing, with typically a frontal (also named coronal or anteroposterior) view, a lateral (or profile) view with the knee in full extension and/or at 20°-30° of flexion, a long-leg view, including the lower limb from the femoral head to the ankle joint and lastly a view of the kneecap at 30° flexion, also called skyline view. From these acquisitions it is possible to build a digital model of the bones F, T to be machined during the operation. A particular knee set of implants I is then selected based on an analysis of the three-dimensional bones F, T model.

The present invention aims at allowing an accurate and safe machining of the bones F, T by means of a surgical system 10 which will be described here-after.

After being established, the bones F, T model is stored in a memory of a control unit 12 of said surgical system 10.

The surgical system 10 includes a 3D imaging sensor 14 which position is well known within the surgical system 10. More precisely, the 3D imaging sensor 14 is placed at a known geometrical position of the lockable unit 20. This 3D imaging sensor 14 allows the operator, in cooperation with the bones F, T model stored in the memory of the control unit 12, to reset the anatomical reference system for each new operation. Once a bones F, T model has been determined for a given patient, and stored inside the memory of the control unit 12, the surgical system 10 can be used for surgery. Once the patient is correctly installed, the anatomical structure A to be seen and the surgery system correctly put in place with regards to the patient, an acquisition of the anatomical structure A is taken. This acquisition is taken with the 3D imaging sensor 14. The control unit 12 analyses the taken acquisition and merges it with the bones F, T model. This enables the control unit 12 to position the anatomical structure A with regards to the 3D imaging sensor 14 and therefore to the surgery system 10. This then enables the control unit 12 to define an anatomical reference system and set the precise machining planes $P_1$, $P_2$, $P_3$, $P_4$, $P_5$, $P_6$ for this specific surgery within this anatomical reference system.

Figure 2A:
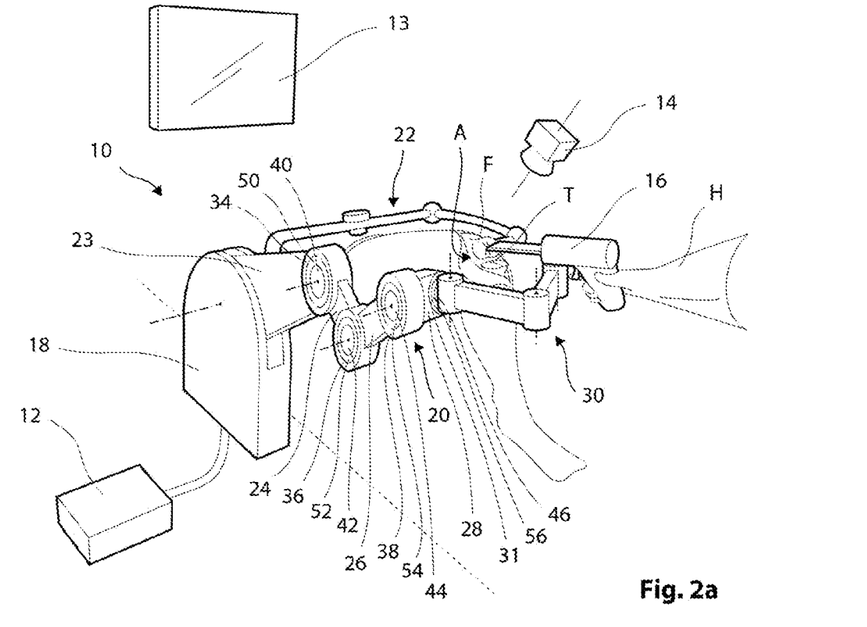
FIG. 2a is a schematic perspective view of a first embodiment of the surgical system in its whole, used by an operator.
Figure 3:
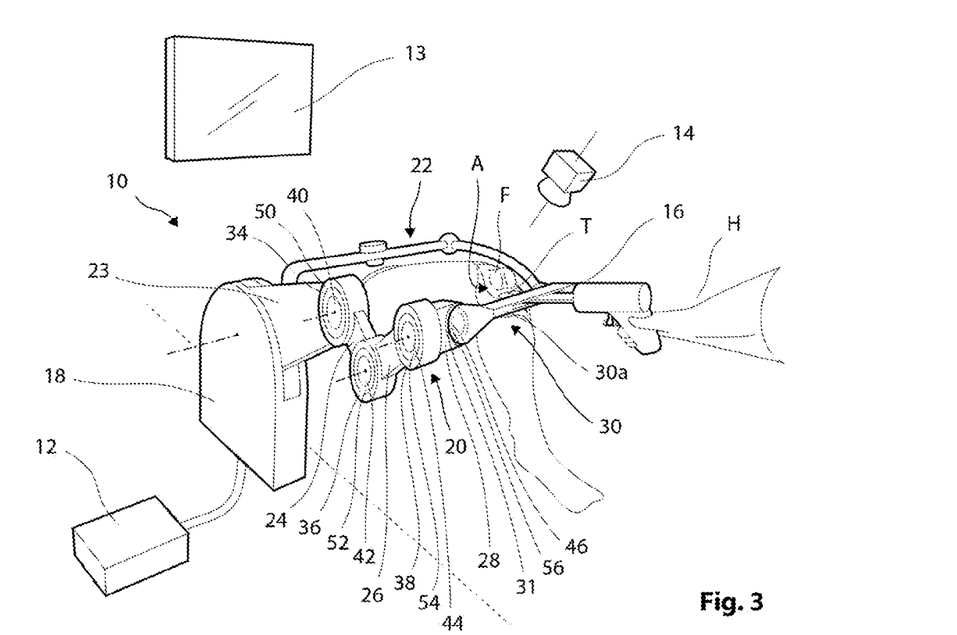
FIG. 3 is a schematic perspective view of a second embodiment of the surgical system in its whole, used by an operator.

After the machining steps, the bones F, T display clean ends with sharp edges in order to facilitate the fitting and fixation of the implant I (see FIGS. 2 and 3).

The free surface of the bones F, T to be machined (see FIG. 2) is limited and there are therefore only a few areas where a machining tool 16 can be put in contact with the bones F, T. This contact has to be as minimally invasive as possible in order to neither damage the bones F, T nor the surrounding soft tissue, while ensuring a precise relative positioning of the machining tool 16 relative to the bones F, T.

Figure 4:
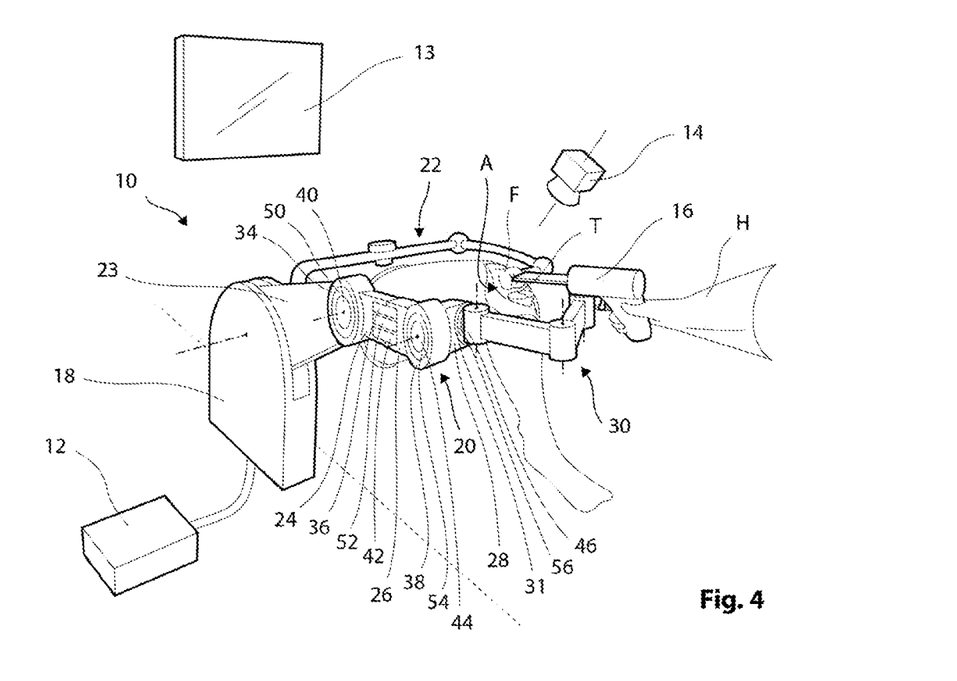
FIG. 4 is a schematic perspective view of a third embodiment of the surgical system in its whole, used by an operator.
Figure 5A:
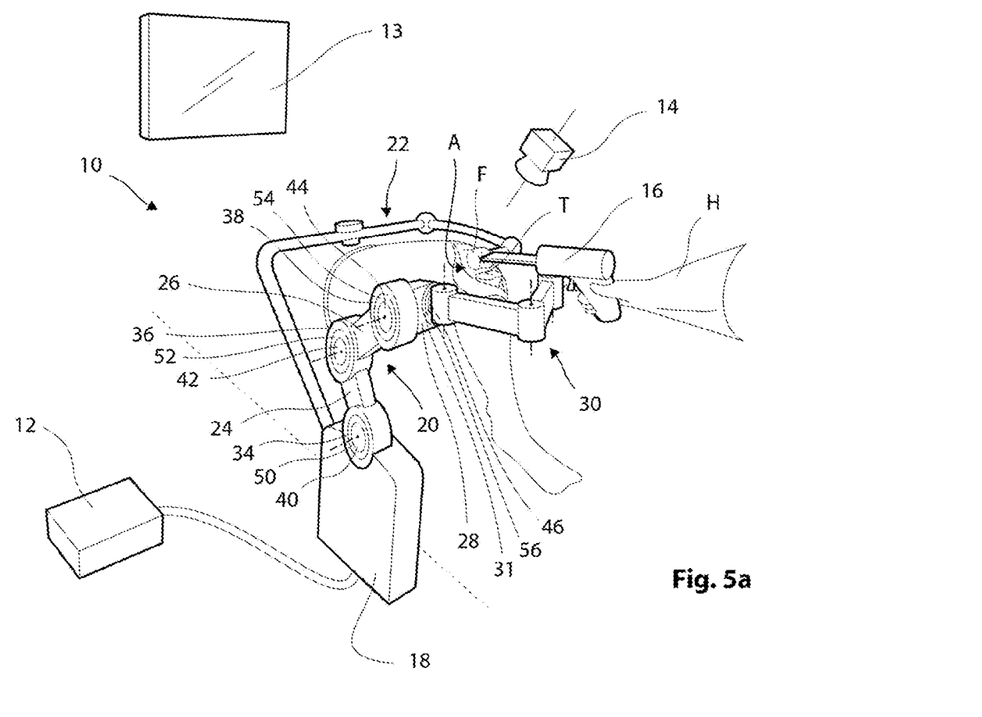
FIG. 5a is a schematic perspective view of a fourth embodiment of the surgical system in its whole, used by an operator.
Figure 5B:
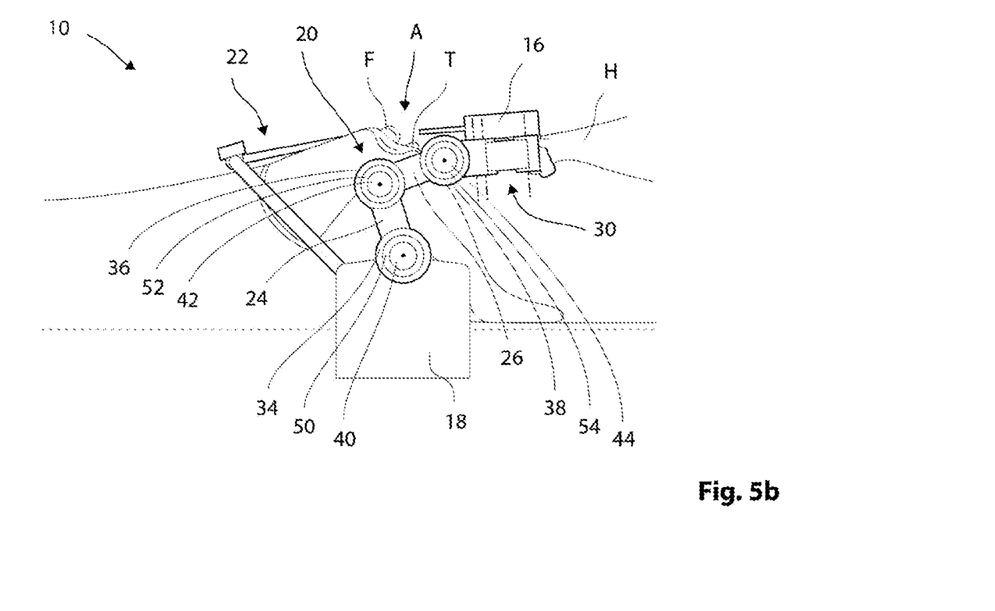
FIG. 5b is a schematic side view of the fourth embodiment of the surgical system in its whole, used by an operator.

The surgical system 10 is to be seen on FIG. 4. As can be seen, said surgical system 10 aims at machining an anatomical structure A (in this case, a knee) of a patient positioned on an operation table. The patient is usually anesthetized and maintained on the operation table by means of specific and well-known fixation means. In addition, the patient's limb in its whole is secured to the surgical system 10.

The surgical system 10 comprises:
a base unit 18 aimed at being secured to the operation table, the machining tool 16 aimed at being manually displaced by the operator, a lockable unit 20, a grasping element 22 designed to secure the anatomical structure A.

The control unit 12 can for example be a computer. This control unit 12 comprises a memory, a real time computing processor, power supply, power converters, fuses, actuators and locking means drivers. The control unit 12 further comprises an operator interface 13 allowing an interaction between the control unit 12 and the operator. This operator interface 13 allows to display real time information such as the machining tool 16 position relative to the anatomical structure A, display the planned implant position and the pre-operative surgical planning in order to help the operator in choosing the best implant and its position, manually configuring a machining target position of the 30.

As can be seen on FIGS. 2a to 5b, the lockable unit 20 and the grasping element 22 are carried by the base unit 18. The base unit 18 is static with regards to the patient. The base unit 18 comprises for example a base secured on the floor or attached to the operation table on which the patient is secured.

In some embodiment (not shown), the base unit 18 is a motorized actuation unit securing the patient's limb. This actuation unit is aimed at enabling a motorized flexion-extension movement of the patient's knee. This actuation unit allows the operator to mobilize the patient's limb and expose the operating field according to the surgical steps.

Figure 6A:
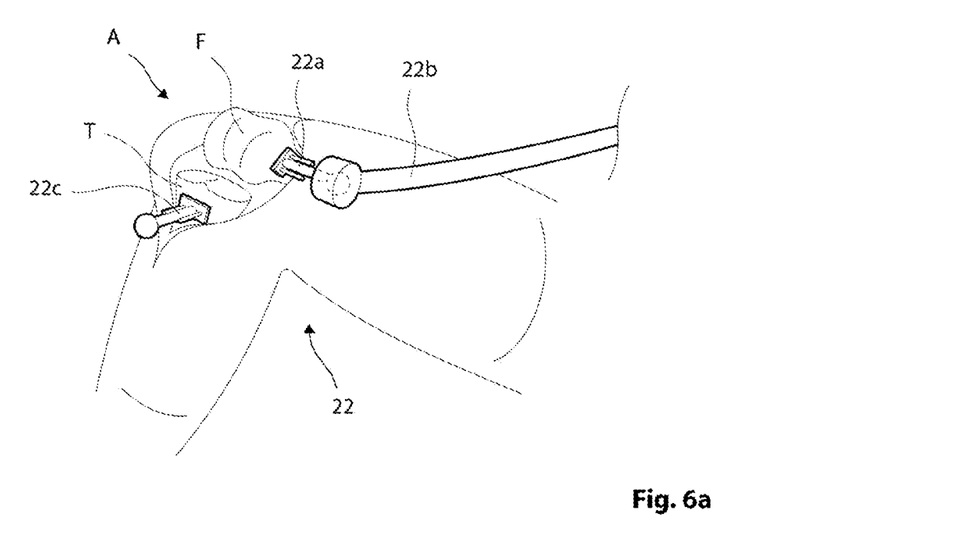
FIG. 6a is a schematic perspective detailed view of the grasping device of the surgical system in a first grasping position.
Figure 6B:
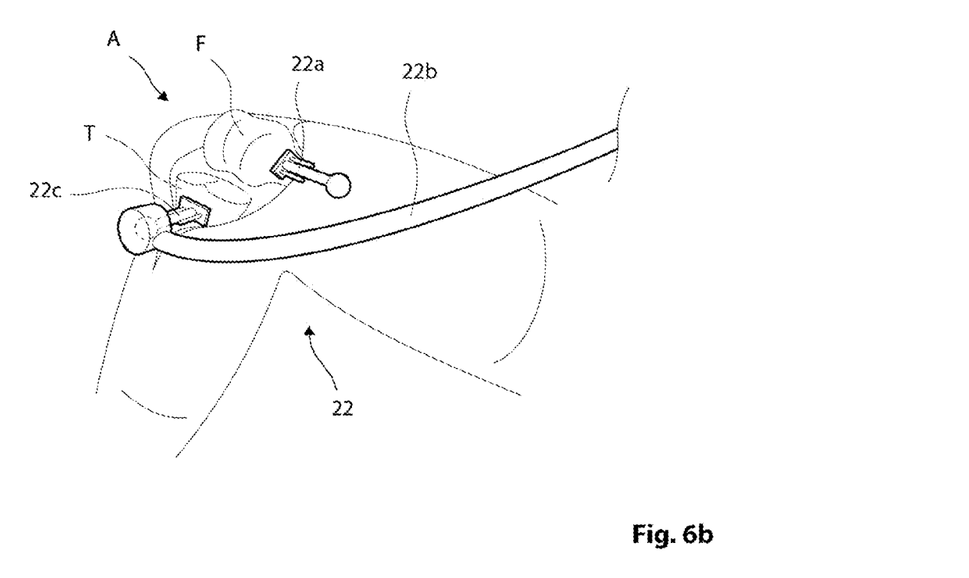
FIG. 6b is a schematic perspective detailed view of the grasping device of the surgical system in a second grasping position.

As can be seen on FIGS. 6a and 6b, the grasping element 22 includes three parts, a first part 22a configured to be rigidly secured to the anatomical structure A, a second part 22b being carried by the base unit 18 and a third part 22c also being configured to be rigidly secured to the anatomical structure A. The first and second parts 22a, 22c are two mobile parts, each aimed at being attached and detached at least two times to the second part 22b. More precisely, each of the first and third parts 22a, 22c of the grasping element 22 parts, is a base plate aimed at being screwed to one bone F, T: each base plate is screwed to one different bone F, T of the anatomical structure A. The second part 22b of the grasping element 22 connects either the first part 22a or the third part 22c. The connection depends on which bone F, T the operator wants to secure. As shown on FIG. 4, the second part is a rod 22b. The grasping element 22 ensures therefore the positioning of the lockable unit 20 with regards to the anatomical structure A while the operator is using the machining tool 16. Particularly, the grasping element 22 secures the femur F while it is machined and secures the tibia T while it is machined. The grasping element 22 enables, while the anatomical structure A is machined, to maintain the machined bone F, T immobile within the patient's flesh. The connection and disconnection of the second part 22b with the first or third part 22a, 22c is enabled by a quick-release system.

Figure 2B:
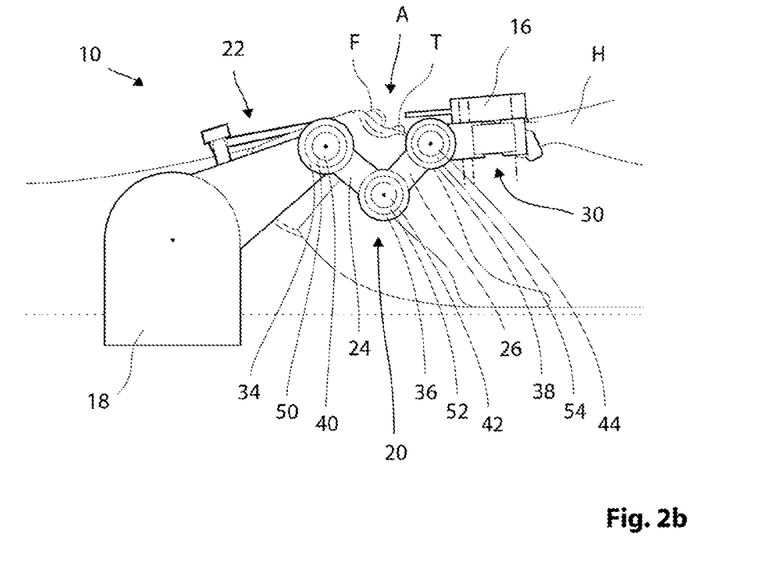
FIG. 2b is a schematic side view of the first embodiment of the surgical system in its whole, used by an operator.
Figure 2C:
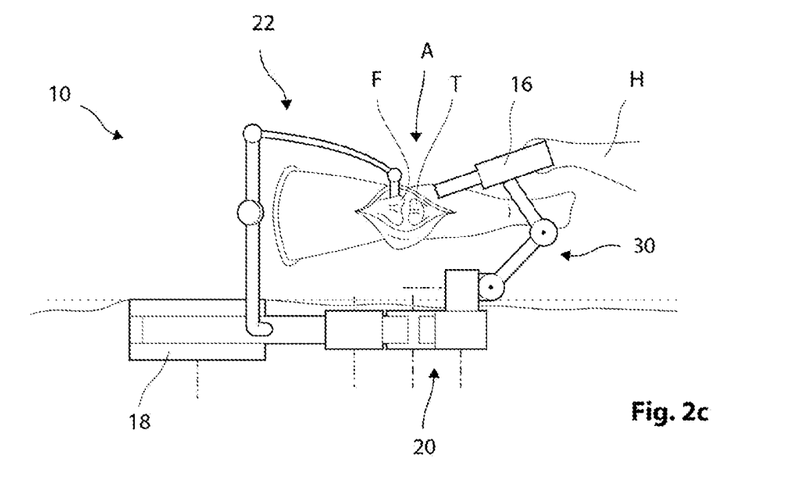
FIG. 2c is a schematic view from above of the first embodiment of the surgical system in its whole, in use.

As can be seen on FIGS. 2a to 2c, the lockable unit 20 comprises at least two linked and manually displaceable elements 23, 24, 26, 28 aimed at being manually moved by an operator's hand H. The manually displaceable elements 23, 24, 26, 28 have to be moved around by the operator. Without the movement induced by the operator, said manually displaceable elements 23, 24, 26, 28 remain motionless. When moved around by an operator, the manually displaceable elements 23, 24, 26, 28 can be arranged according to at least one, relatively to the anatomical structure A, calculated locked configuration $L_1, L_2, L_3, L_4, L_5, L_6$. The configuration $L_1, L_2, L_3, L_4, L_5, L_6$ is calculated by the control unit 12 each manually displaceable element 23, 24, 26, 28 of the lockable 20 unit has therefore a determined position within the calculated locked configuration $L_1, L_2, L_3, L_4, L_5, L_6$ of the lockable unit 20.

As already mentioned, different machining planes $P_1, P_2, P_3, P_4, P_5, P_6$ are determined computer wise during a pre-operative surgical planning Therefore, the corresponding ideal relative position of the machining tool 16 is also determined computer wise. Each machining plane $P_1, P_2, P_3, P_4, P_5, P_6$ thus represents a target position of the machining tool 16 in the anatomical reference system and each machining plane $P_1, P_2, P_3, P_4, P_5, P_6$ corresponds to a specific calculated locked configuration $L_1, L_2, L_3, L_4, L_5, L_6$ of the lockable unit 20. Each plan $P_1, P_2, P_3, P_4, P_5, P_6$ represents a target position of the machining tool 16 in the anatomical reference system and to each plan $P_1, P_2, P_3, P_4, P_5, P_6$ corresponds a specific calculated locked configuration $L_1, L_2, L_3, L_4, L_5, L_6$.

The lockable unit 20 further comprises a constraining device 30 aimed at supporting and guiding the machining tool 16. The constraining device 30 sets the machining plane $P_1, P_2, P_3, P_4, P_5, P_6$ within which the tool 16 can be moved by the operator. Regarding the current invention, the constraining device 30 can carry or guide any kind of tool 16, for example a saw, a drill or a burr. In the example of FIGS. 2a to 5b, the carried machining tool 16 is an oscillating saw. This constraining device 30 is linked to the lockable unit 20 by means of an articulated connection 31. This articulated connection 31 can be a quick fastener.

In the embodiment of FIGS. 2a, 2b, 2c, 4, 5a and 5b, this constraining device 30 is a planar mechanism.

It is well known by any person skilled in the art that, according to the relative motion of the rigid bodies, mechanisms can be divided into planar mechanisms and spatial mechanisms. In a planar mechanism, all of the relative motions of the rigid bodies are in one plane or in parallel planes. If there is any relative motion that is not in the same plane or in parallel planes, the mechanism is called spatial mechanism. In other words, planar mechanisms are essentially two dimensional while spatial mechanisms are three dimensional.

The planar mechanism as illustrated on FIGS. 2a, 2c, 4 and 5a is a passive mechanism that needs to be actuated by the operator's hand H. The planar mechanism defines the machining plane $P_1, P_2, P_3, P_4, P_5, P_6$ by blocking the machining tool 16 within a determined orientation. Once blocked, the machining tool 16 can only be moved according to three degrees of freedom within the machining plane $P_1, P_2, P_3, P_4, P_5, P_6$. The planar mechanism might include encoders linked to the control unit 12. This would allow the control unit 12 to precisely know the configuration of the planar mechanism. The control unit 12 might be able to help the operator to operate the machining tool 16 by means of haptic, visual or audio signals.

On another embodiment illustrated on FIG. 3, the constraining device 30 is a guiding element comprising a slit or a sleeve 30a forming a cutting guide through which an active and elongated part of the machining tool 16, for example the blade, can be inserted. This slit or sleeve 30a orientates the machining tool 16 and confines it within the predetermined machining plane $P_1, P_2, P_3, P_4, P_5, P_6$. In another embodiment (not shown), the constraining device 30 can be tracked. The machining tool 16 can be secured in a removable or unremovable way to the constraining device 30. The constraining device 30 is linked to the lockable unit 20 by means of an articulated connection 31. As already mentioned, this articulated connection 31 can be a quick fastener. The lockable unit 20 of the surgical system 10 comprises six locked configurations $L_1, L_2, L_3, L_4, L_5, L_6$. The memory of the control unit 12 contains a recording of each of the calculated locked configurations $L_1, L_2, L_3, L_4, L_5, L_6$ of the lockable unit 20. In short, the lockable unit 20 aims at positioning the constraining device 30 relatively to the anatomical structure A to enable the machining tool 16 to machine said anatomical structure A. Each calculated locked configuration $L_1, L_2, L_3, L_4, L_5, L_6$ of the lockable unit 20 corresponds to a unique machining plane $P_1, P_2, P_3, P_4, P_5, P_6$. Each locked configuration $L_1, L_2, L_3, L_4, L_5, L_6$ constraining the machining tool 16 within said corresponding unique machining plane $P_1, P_2, P_3, P_4, P_5, P_6$.

Each calculated locked configuration $L_1, L_2, L_3, L_4, L_5, L_6$ of the lockable unit 20 is defined within an anatomical reference system (re)set by means of the 3D imaging sensor 14. However, each time the grasping element 22 is secured to the anatomical structure A, the 3D imaging sensor 14 makes new acquisitions of the anatomical structure A in order to verify that the anatomical structure is still in place. If the anatomical structure A has moved the control unit 12 recalculates the remaining locked configurations $L_1, L_2, L_3, L_4, L_5, L_6$, in order to fit the machining planes $P_1, P_2, P_3, P_4, P_5, P_6$ to the position of the anatomical structure A.

As can be seen on FIGS. 2a to 5b, the manually displaceable elements 23, 24, 26, 28 of the lockable unit 20 are linked to each other by at least one degree of freedom. In the embodiment shown on FIGS. 2a, 2b, 2c, 3 and 4, there are four manually displaceable elements 23, 24, 26, 28 to be counted. On the embodiment illustrated by FIGS. 5a and 5b, there are three manually displaceable elements 24, 26, 28 to be counted. On the embodiments illustrated on FIGS. 2a, 2b, 2c, 3, 5a and 5b the manually displaceable elements 23, 24, 26, 28 are all linked to each other by means of articulated connections 34, 36, 38. In the embodiment illustrated on FIG. 4, the second and third manually displaceable elements 24, 26 are linked to each other by a sliding connection while the other manually displaceable elements 23, 24, 26, 28 are linked of each other by means of an articulated connection 36, 38. In each embodiment, the combination of the manually displaceable elements 23, 24, 26, 28 and the connecting degrees of freedom (articulated connections 34, 36, 38 or sliding connections) forms a planar linkage mechanism. The three (as on FIGS. 5a, 5b) or four (as on FIGS. 2a, 2b, 2c, 3, 4) manually displaceable elements 23, 24, 26, 28 are all oriented in the same direction and this orientation does not change during the manually induced motion: said manually displaceable elements 23, 24, 26, 28 remain within a plan substantially parallel to the operation table edge and therefore parallel to the patient's limb.

As previously mentioned, the different degrees of freedom (sliding or articulated connections 34, 36, 38) allow the operator to displace the manually displacing elements 23, 24, 26, 28 and bring the lockable unit 20 into the calculated locked configuration $L_1, L_2, L_3, L_4, L_5, L_6$ corresponding to the pre-determined machining plane $P_1, P_2, P_3, P_4, P_5, P_6$ needed by the operator.

The rotation axis of the articulated connection 31 of the constraining device 30 is extending sensibly perpendicularly to the rotation axes of the sliding or articulated connections 34, 36, 38 of the lockable unit 20.

The surgical system 10 further comprises a sensor unit 32. The sensor unit 32 includes at least one sensor 40, 42, 44, 46 aimed at following, in real time, a real time configuration of the lockable unit 20 within the anatomical reference system.

The sensor unit 32 is connected to the control unit 12 and aims at estimating the configuration of the lockable unit 20 relative to the femur F or the tibia T. In the embodiment shown on figure, the sensor unit 32 comprises several mechanical sensors 40, 42, 44, 46 mounted within the sliding or articulated connections 31, 34, 36, 38 and enabling the control unit 12 to follow the position of each manually displaceable element 23, 24, 26, 28. When the detected angular position of the articulated connections 31, 34, 36, 38 or the relative position of the manually displaceable elements 23, 24, 26, 28 corresponds to a calculated locked configuration $L_1, L_2, L_3, L_4, L_5, L_6$ stored in the memory of the control unit 12, the control unit 12 outputs a signal. This signal can be an acoustic, visual or vibrating signal informing the operator about the reaching of a calculated locked configuration $L_1, L_2, L_3, L_4, L_5, L_6$. Based on this signal, the operator may perform a manual lock of the articulated connections 31, 34, 36, 38 and lock the lockable unit 20. However, in a preferred embodiment illustrated on FIGS. 2a, 2b, 2c, the signal emitted by the control signal is an electrical signal. This electric signal communicates directly with the sliding or articulated connections 31, 34, 36, 38 by means of locking means 50, 52, 54, 56.

Each sliding or articulated connection 31, 34, 36, 38 is cooperating with locking means 50, 52, 54, 56. In the present embodiment those locking means 50, 52, 54, 56. are locking joints or brakes. Each locking means 50, 52, 54, 56 is connected to the control unit 12 and is configured to be activated by the control unit 12. This activation takes place when the control unit 12 sense, through the sensor unit 32, that the real time configuration of the lockable unit 20 corresponds one of the predetermined calculated locked configuration $L_1, L_2, L_3, L_4, L_5, L_6$ recorded inside the memory of the control unit 12.

This activation locks the sliding or articulated connections 31, 34, 36, 38 and therefore locks the constraining device 30 in a predetermined position which constrains the machining tool 16 within one of the predetermined corresponding machining planes $P_1, P_2, P_3, P_4, P_5, P_6$. This way, the operator is informed when the right locked configuration $L_1, L_2, L_3, L_4, L_5, L_6$ of the lockable device 20 is reached and is informed that there is no need to further try to move the manually displaceable elements 23, 24, 26, 28. The operator then knows that the bone F, T machining according to the corresponding machining plane $P_1, P_2, P_3, P_4, P_5, P_6$ can begin. In one embodiment, the locking means remain manually lockable in case of an emergency. The signal emitted by the control unit 12 can be a double signal: a visual or acoustic or vibrating signal aimed at the operator and an electric signal directed to the locking means 50, 52, 54, 56. Therefore, the operator gets some information about when the calculated locked configuration $L_1, L_2, L_3, L_4, L_5, L_6$ is about to be reached. For this purpose, the signal may have a frequency and/or modulation and/or intensity varying according to the discrepancy to the locked configuration $L_1, L_2, L_3, L_4, L_5, L_6$. The signal may be a haptic signal, a sound signal or a visual signal.

In an embodiment, the control unit 12 activates each lockable means in a progressive way: the activation of each locking means 50, 52, 54, 56 is reversely proportional to the distance separating each manually displaceable element 23, 24, 26, 28 from its predetermined position within the locked configuration $L_1, L_2, L_3, L_4, L_5, L_6$. This allows the operator to feel when the locked configuration $L_1, L_2, L_3, L_4, L_5, L_6$ is soon to be reached and allows to secure the moving of the lockable unit 20. Regarding another aspect of the locking, the control unit 12 may activate the locking means 50, 52, 54, 56 one by one according to an order recorded inside the memory of control unit 12. The first locking means 50, 52, 54, 56 to be activated is the locking means 50, 52, 54, 56 cooperating with the articulated connection 34 the closest to the base unit 18. Once this first articulated connection 34 is locked, the control unit activates the second closest to the base unit 18 articulated connection 36. The last articulated connection to be activated is the connection 31 which connects the constraining device 30 to the lockable unit 20. Further, the control unit 12 contains at least two locked configurations $L_1$, $L_2$, $L_3$, $L_4$, $L_5$, $L_6$ recordings. In the current invention, the control unit 12 contains six different locked configurations $L_1$, $L_2$, $L_3$, $L_4$, $L_5$, $L_6$ recordings. Those calculated locked configurations $L_1$, $L_2$, $L_3$, $L_4$, $L_5$, $L_6$ are recorded inside the control unit 12 following a given chronological order. This chronological order is determined by the operator, during the pre-operative phase. The control unit 12 is configured to activate the locking means 50, 52, 54, 56 according to each calculated locked configuration $L_1$, $L_2$, $L_3$, $L_4$, $L_5$, $L_6$ following this chronological order.

Figure 7:
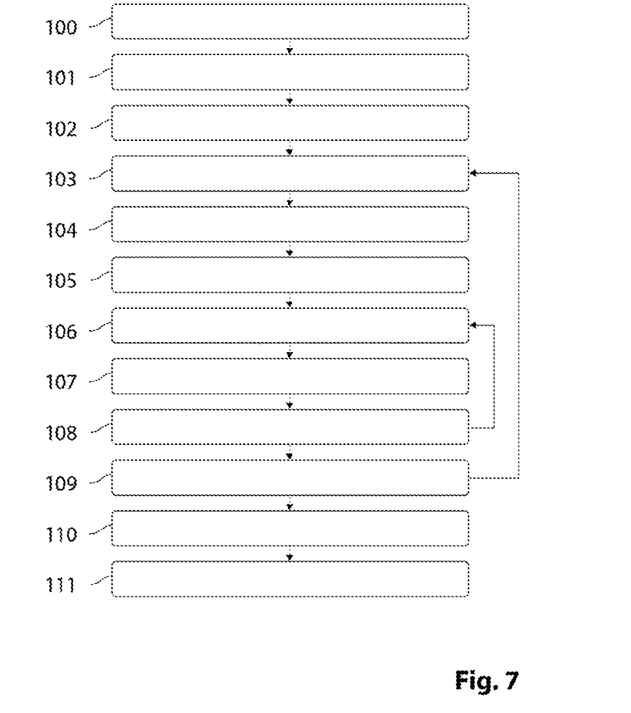
FIG. 7 is a flowchart of a complete surgical intervention leaded by means of the surgical system according to the invention.

FIG. 7 is a flowchart of a complete surgical intervention intended to machine an anatomical structure A using the surgical system 10 in order to perform a total knee arthroplasty:

- at first, during step 100, the surgical system 10 is installed and the base unit 18 is secured in a stationary way relative to the patient, for example clamped to the operation table and/or on a patient's limb positioner that maintains the patient's limb during surgery;
- at step 101, the operator secures the grasping element 22 to the femur F, in an area where no machining will be performed. The first part 22a of the grasping element 22 can be secured by screwing into the femur F. It may also be secured through a grasping mechanism or chemical material;
- at step 102, the exposed patient's femur F and the grasping element 22 are acquired by the 3D imaging sensor;
- at step 103, the Femur F is located and registered to the pre-operative planning data stored inside the memory of the control unit 12. Pre-operative surgical planning is transposed from the virtual referential to the real surgical scene. The control unit 12 computes the position of the machining planes $P_1$, $P_2$, $P_3$, $P_4$, $P_5$, $P_6$ based on the pre-operative model and submits it for the surgeon's validation through the user interface 13;
- at step 104, the control unit 12 calculates the locked configurations $L_1$, $L_2$, $L_3$, $L_4$, $L_5$, $L_6$ corresponding to each respective machining plane $P_1$, $P_2$, $P_3$, $P_4$, $P_5$, $P_6$;
- at step 105, the operator manually moves the lockable unit 20 towards the first locked configuration $L_1$. A signal, haptic or otherwise, provides feedback during the movement and, when the first articulated connection 34 is approaching its determined position within the first locked configuration $L_1$, the locking unit 20 gradually becomes stiffer, forcing the operator to slow down the motion. Once the first articulated connection has reached its calculated position within the locked configuration $L_1$ is reached, the lockable unit 20 locks and the first articulated connection becomes completely stiff. The operator follows the same procedure for the other articulated connections;
- in step 106, the constraining device 30, in this case a planar mechanism, is aligned with the first machining plane $P_1$. The control unit 12 indicates to the operator that the machining can start by means of a signal or a technical release of the machining tool 16;
- in step 107, the operator performs the machining by moving the machining tool 16 within the degrees of freedom allowed by the constraining device 30;
- in step 108 (a verification step), the patient's femur F is acquired again, following the same procedure as in step 102, in order to validate the accuracy of the machining with respect to the pre-operative surgical planning Corrections can be performed by updating the planning, i.e. returning to step 104;
- the steps 105 to 108 are performed until completion of the machining planned on the femur F;
- the steps 102 to 108 are performed again on the tibia T for the machining planned on the tibia T.

It is to be noticed that the present surgical system 10 allows any operator to operate in complete safety as any induced movement is manually induced and that solely the locking is automatically induced. The operator remains therefore in complete control of the procedure. Further, using an anatomical reference system based on a model defined prior to the incision, reduces the operation duration and reduces the invasiveness of said operation. The reduction of the operation duration is an important issue because the risks of infection, anesthesia sequelae, and sequelae related to the tourniquet are positively correlated with said duration.

The invention claimed is:

1. A surgical system for machining an anatomical structure of a patient positioned on an operation table, said anatomical structure being part of an anatomical reference system of the surgical system, said surgical system comprising:
   - a base unit aimed at being secured to the operation table,
   - a machining tool aimed at being manually displaced by an operator,
   - a lockable unit carried by the base unit, said lockable unit including:
     - at least two linked and manually displaceable elements aimed at being manually arranged according to a least one, relatively to the anatomical structure, calculated locked configuration, said locked configuration being defined within the anatomical reference system, and
     - a constraining device aimed at supporting and guiding the machining tool,
   - a grasping element carried by the base unit, said grasping element being designed to secure the anatomical structure,
   - a sensor unit including at least one sensor aimed at following, in real time, a real time configuration of the lockable unit within the anatomical reference system,
   - a control unit containing a recording of the at least one locked configuration of the lockable unit,
   where the at least two elements of the lockable unit are linked to each other by at least one degree of freedom aimed at cooperating with lockable means, said lockable means being configured to be activated by the control unit when the real time configuration of the lockable unit corresponds to the at least one locked configuration recorded inside the control unit, in order to lock the constraining device in a determined position which constrains the machining tool within a determined machining plane.

2. The surgical system according to claim 1, wherein the control unit is configured to activate each locking means in a progressive way.

3. The surgical system according to the claim 2, wherein each displaceable element of the lockable unit has a determined position within the locked configuration of the lockable unit, the activation of each locking means being reversely proportional to a distance separating each displaceable element from its determined position.

4. The surgical system according to claim 1, wherein the locking means are activated one by one according to a predetermined order recorded inside the control unit.

5. The surgical system according to claim 4, wherein the control unit contains at least two locked configurations, said at least two locked configurations being recorded inside the control unit according to a given chronological order, the control unit being configured to activate the locking means according to each locked configuration following the chronological order.

6. The surgical system according to claim 5, wherein each locked configuration of the lockable unit corresponds to a unique machining plane, each locked configuration constraining the machining tool within said corresponding unique machining plane.

7. The surgical system according to claim 1, wherein the constraining device is a planar mechanism.

8. The surgical system according to claim 1, wherein the constraining device is a cutting guide.

9. The surgical system according to claim 1, wherein the grasping element includes at least two parts, a first part configured to be rigidly secured to the Femur of the anatomical structure, and a second part being carried by the base unit, said first part being a mobile part aimed at being attached and detached at least two times to the second part.

10. The surgical system according to claim 9, wherein the grasping element includes a third part, said third part also being configured to be rigidly secured to the Tibia of the anatomical structure, said third part being another mobile part aimed at being attached and detached at least two times to the second part.

11. The surgical system according to claim 10, wherein the anatomical structure includes a first bone and a second bone, the first part of the grasping element being configured to be secured to the first bone and the third part of the grasping element being configured to be secured to the second bone.

12. The surgical system according to claim 9, wherein the second part of the grasping element connects either the first part or the third part.

* * * * *